United States Patent

Ondetti et al.

[11] 4,313,948
[45] Feb. 2, 1982

[54] HYPOTENSIVE IMIDAZOLE SUBSTITUTED MERCAPTO-1-OXOPROPYL-L-PROLINES

[75] Inventors: Miguel A. Ondetti; Denis E. Ryono, both of Princeton, N.J.

[73] Assignee: E. R. Squibb & Sons, Inc., Princeton, N.J.

[21] Appl. No.: 208,739

[22] Filed: Nov. 20, 1980

[51] Int. Cl.³ .................. A61K 31/415; C07D 403/06
[52] U.S. Cl. ............................ 424/273 R; 260/326.4; 542/427; 548/336; 548/341; 548/342
[58] Field of Search ..................... 548/336; 424/273 R

[56] References Cited

U.S. PATENT DOCUMENTS

| | | | |
|---|---|---|---|
| 4,105,776 | 8/1978 | Ondetti et al. | 424/274 |
| 4,154,935 | 5/1979 | Ondetti et al. | 546/189 |
| 4,154,946 | 5/1979 | Ondetti et al. | 548/336 X |
| 4,217,359 | 8/1980 | Krapcho | 424/274 |
| 4,248,883 | 2/1981 | Sawayama et al. | 548/336 X |
| 4,264,620 | 4/1981 | Iwao et al. | 548/336 X |

OTHER PUBLICATIONS

Iwao, et al., U. K. Patent Application GB2027025A.
Ondetti, et al., U. K. Patent Application GB2028327A.
Bestmann, et al., Angew. Chem., 73, 27 (1961).
Pyman, J. Chem. Soc., 186 (1916).
Ehler, K., *J. Org. Chem.*, 41 (18), 3041–3042 (1976).

*Primary Examiner*—Richard A. Schwartz
*Attorney, Agent, or Firm*—Lawrence S. Levinson; Stephen B. Davis

[57] ABSTRACT

The invention relates to new compounds useful as hypotensive agents, of the formula:

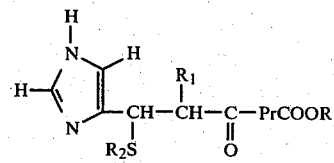

wherein
R is hydrogen or lower alkyl;
$R_1$ is hydrogen, lower alkyl or halo substituted lower alkyl;
$R_2$ is hydrogen,

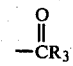

or
$R_3$ is lower alkyl, phenyl or phenyl lower alkyl;
Pr—COOR is a substituted or unsubstituted proline.

6 Claims, No Drawings

HYPOTENSIVE IMIDAZOLE SUBSTITUTED MERCAPTO-1-OXOPROPYL-L-PROLINES

BACKGROUND OF THE INVENTION

Ondetti et al. in U.S. Pat. No. 4,105,776 disclose proline derivatives having the formula

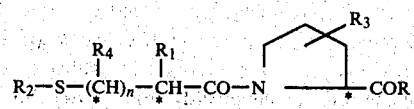

wherein
n is 0, 1 or 2;
$R_2$ is hydrogen, acyl, etc.;
R is hydroxy, $NH_2$ or lower alkoxy;
$R_1$ and $R_4$ each is hydrogen, lower alkyl, phenyl or phenyl-lower alkyl;
$R_3$ is hydrogen, hydroxy or lower alkyl.

Ondetti et al. in U.S. Pat. No. 4,154,935 disclose halogenated compounds which have the general formula

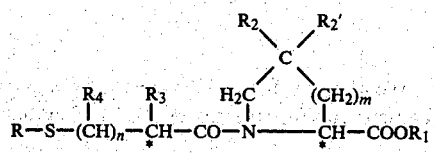

wherein R is hydrogen lower alkanoyl or

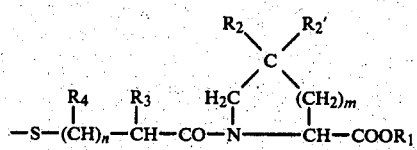

$R_1$ is hydrogen or lower alkyl;
$R_2$ and $R_2'$ each is hydrogen or halogen;
$R_3$ and $R_4$ each is hydrogen, lower alkyl or trifluoromethyl not more than one being trifluoromethyl, and at least one of $R_2$, $R_2'$,
$R_3$ or $R_4$ is a halogen or trifluoromethyl substituent represented by the named symbol as defined above;
m is 1 or 2; and
n is 0 or 1.

Iwao et al. in U.K. patent application GB 2027025 A disclose compounds of the formula

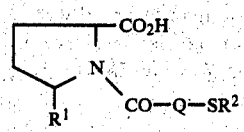

wherein
$R_1$ is phenyl, hydroxyphenyl mercapto-lower alkyl, higher alkyl, higher alkenyl, cycloalkyl, aralkyl, aralkenyl, substituted cycloalkyl, substituted aralkyl, substituted aralkenyl, substituted phenyl, substituted napthyl,
$R_2$ is hydrogen or benzoyl; and
Q is a straight or branched chain alkylene with 1 to 3 carbon atoms.

Ondetti et al. in U.K. patent application GB 2028327 A disclose compounds of the formula

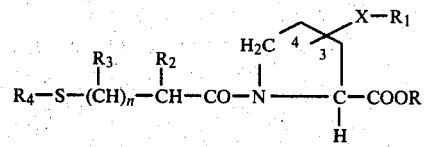

$X-R_1$ is located at the 3- or 4- position of the proline ring;
X is oxygen or sulfur;
R is hydrogen or lower alkyl;
$R_1$ is lower alkyl, lower alkenyl, lower alkynyl, phenyl, substituted phenyl, phenyl-lower alkelene, or substituted phenyl-lower alkylene;
$R_2$ and $R_3$ are independently selected from hydrogen, lower alkyl and trifluoromethyl;
$R_4$ is hydrogen,

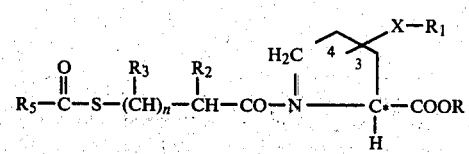

$R_5$ is lower alkyl phenyl, or phenyl-lower alkylene; and
n is 0, 1 or 2.

SUMMARY OF THE INVENTION

The invention relates the new compounds which have the general formula:

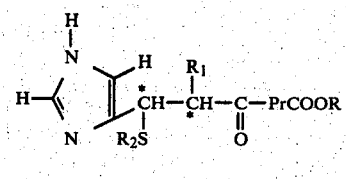

wherein
R is hydrogen or lower alkyl;
$R_1$ is hydrogen, lower alkyl or halo substituted lower alkyl;
$R_2$ is hydrogen,

or

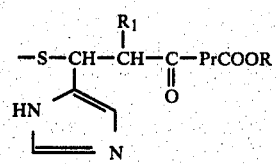

$R_3$ is hydrogen, lower alkyl, phenyl or phenyl lower alkyl;
Pr-COOR is a substituted or unsubstituted proline of the structure

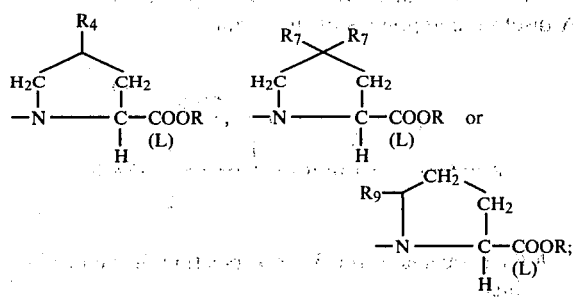

R$_4$ is hydrogen, lower alkyl, hydroxy, halogen, keto, azido, cycloalkyl, phenyl, substituted phenyl, phenyl-lower alkyl, substituted phenyl-lower alkyl,

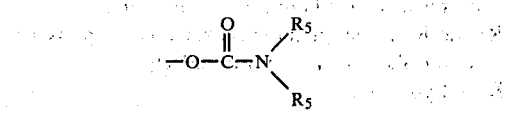

or Y-R$_6$;

R$_5$ is hydrogen or lower alkyl;

Y is oxygen or sulfur;

R$_6$ is lower alkyl, lower alkenyl, lower alkynyl, phenyl, substituted phenyl, phenyl-lower alkyl, substituted phenyl-lower alkyl, 1- or 2-naphthyl, substituted 1- or 2-naphthyl, biphenyl, or substituted biphenyl;

R$_7$ is halogen or -Y-R$_8$;

R$_8$ is lower alkyl, phenyl, phenyl-lower alkyl, substituted phenyl-lower alkyl, biphenyl, 1- or 2-naphthyl, substituted 1- or 2-naphthyl, substituted biphenyl or the R$_8$ groups join to complete an unsubstituted 5- or 6-membered ring or such ring wherein a carbon atom is substituted by a lower alkyl or di(-lower alkyl) group;

R$_9$ is keto, phenyl, 2- or 4-hydroxyphenyl; and salts of the formula I compounds.

The (L) in the above structures indicates a center of asymmetry which is in the L-configuration.

The asterisks indicate asymmetric carbon atoms. The carbon at R$_1$ in the acyclic side chain is asymmetric when R$_1$ is other than hydrogen.

DETAILED DESCRIPTION OF THE INVENTION

The invention in its broadest aspect relates to the compounds of formula I above and to salts thereof, to compositions containing such compounds and to the method for using such compounds as anti-hypertensive agents.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The C$_1$–C$_4$ members and especially the C$_1$ and C$_2$ members, are preferred.

The term lower alkoxy includes such lower alkyl groups bonded through an oxygen and the term lower alkyl thio includes such lower alkyl groups bonded through a sulfur.

The halogens are chlorine, bromine and fluorine; chlorine and fluorine being preferred.

The term cycloalkyl refers to saturated rings of 3 to 7 carbon atoms with cyclohexyl being most preferred. The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term phenyl-lower alkyl includes a phenyl ring attached to a lower alkyl group as defined above. Phenylmethyl and phenylethyl are preferred.

The term substituted phenyl and substituted phenyl-lower alkyl include such groups wherein the phenyl ring has a lower alkyl, preferably methyl, lower alkoxy, preferably methoxy, lower alkylthio, preferably methylthio, Cl, Br, F, or hydroxy substituent. When the substituent is methyl, methoxy, Cl or F the phenyl ring may be di or trisubstituted.

To form a compound of formula I an acid of the formula

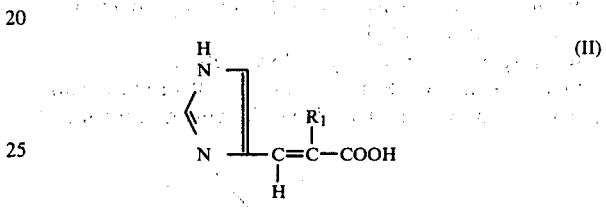

is reacted with di-tert-butyl carbonate to form the t-butyloxycarbonyl (represented as BOC) of the formula: (III)

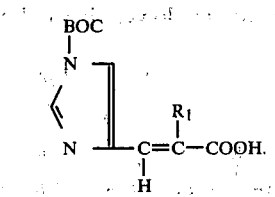

Then the formula III compound is treated with p-nitrophenol (represented as OPNP) to form the compound of the formula:

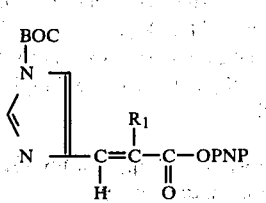

A substituted or unsubstituted proline represented as PrCOOR and defined above (wherein R is t-butyl) is then reacted with the formula IV compound to form a compound of the formula:

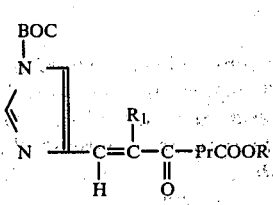

By treating the compound of formula V with

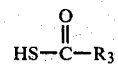

wherein R₃ is as defined above, a compound of the formula:

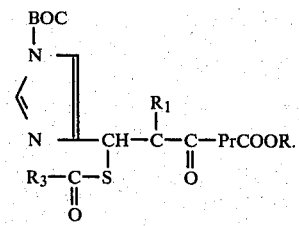

is formed.

The compound of formula VI is then treated with hydrochloric acid to form a compound of the formula:

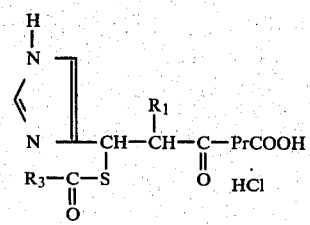

The formula I compounds wherein R₂ is hydrogen is formed by treating the compounds of formula VII with NaOH in aqueous solution.

Various substituted prolines are disclosed by Mauger et al., Chem. Review, Vol. 66, p 47–86 (1966). Ondetti et al. disclose various alkyl, halogen, ether and thioether substituted prolines in U.S. Pat. Nos. 4,105,776, 4,154,935 and U.K. application 2,028,327. Iwao et al. in U.K. application 2,027,025 disclose various 5-substituted prolines.

As disclosed by Krapcho in U.S. Pat. No. 4,217,359, the carbamoyloxy substituted prolines can be obtained by reacting the hydroxy substituted N-protected proline with phosgene and then the amine HN(R₅)₂. R₅ is as defined above. Removal of the N-protecting group yields the desired starting material.

As disclosed by Krapcho in U.S. Ser. No. 99,164, the prolines of the formula

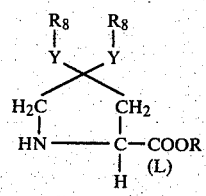

(wherein R and R₈ are as defined above) can be prepared by reacting the keto compound of the formula

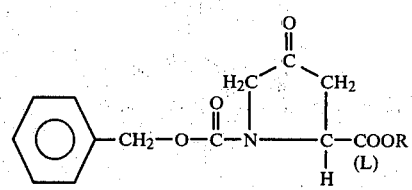

(wherein R is as defined above) with an alcohol or thiol having the formula $$R_8\text{-}Y\text{-}H \quad (X)$$

(wherein R₈ and Y are as defined above) in the presence of an orthoformate or thioformate of the formula HC(Y-R₈)₃ and an acid such as concentrated sulfuric acid or p-toluenesulfonic acid. Removal of the carbobenzyloxy group by catalytic hydrogenation when Y is oxygen or by treatment with HBr and acetic acid when Y is sulfur yields the desired starting material. The spiro substituted prolines can be prepared in a similar manner by reacting the keto compound of formula IX with the alcohol or thiol of the formula

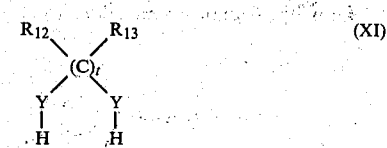

wherein t is 2 or 3 and R₁₂ and R₁₃ are independently selected from hydrogen and lower alkyl. This reaction is performed in the presence of p-toluenesulfonic acid and removal of the carbobenzyloxy group yields the desired starting material. When either or both R₁₂ and R₁₃ are lower alkyl it is preferred that the substituted proline of formula VIII be treated directly with a molar excess of the alcohol or thiol of formula XI.

As disclosed by Krapcho in U.S. Ser. No. 164,985 filed July, 1, 1980 the 4-substituted proline starting materials wherein the substituent R₄ is cycloalkyl, phenyl, substituted phenyl, phenyl-lower alkyl, or substituted phenyl-lower alkyl can be prepared by reacting the 4-keto proline of formula IX with a solution of the Grignard or lithium reagent (XII) R₄-Mg-halo or R₄-Li wherein halo is Br or Cl to yield

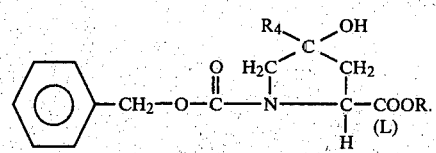

This compound is treated with a dehydrating agent such as p-toluenesulfonic acid, sulfuric acid, potassium bisulfate, or trifluoroacetic acid to yield the 3,4-dehydro-4-substituted proline of the formula

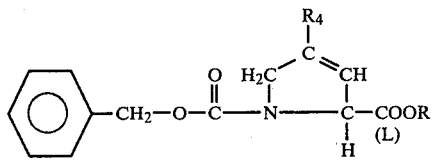 (XIV)

Removal of the N-benzyloxycarbonyl protecting group and hydrogenation of the compound of formula XIV yields the desired starting materials. The substituted proline wherein $R_4$ is cyclohexyl can be prepared by further hydrogenation of the 4-phenyl proline compound.

Acids of formula II may be formed by reacting a compound of the formula

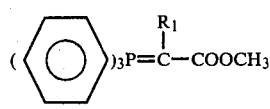 (XV)

with imidazole-4-carboxaldehyde in absolute ethanol, followed by treatment with sodium hydroxide.

Preferred compounds of this invention with respect to the proline portion of the structure of formula I are those wherein:

$R_4$ is hydrogen, lower alkyl, cyclohexyl,

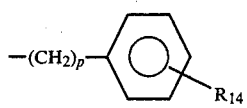

or $Y-R_6$.

$R_6$ is lower alkyl of 1 to 4 carbons,

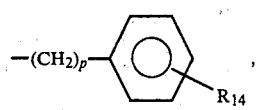, a substituted or unsubstituted 1- or 2-naphthyl of the formula

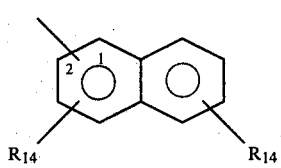

or a substituted or unsubstituted biphenyl of the formula

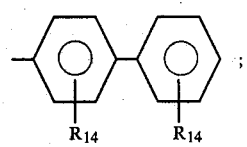;

p is zero, one or two;
$R_{14}$ is hydrogen, methyl, methoxy, methylthio, Cl, F, Br, or hydroxy;

$R_7$ is Cl, F, or $-Y-R_8$;
$R_8$ is lower alkyl of 1 to 4 carbons or the $R_8$ groups join to complete an unsubstituted 5- or 6-membered ring or said ring in which one or more of the carbons has a methyl or dimethyl substituent;
$R_9$ is phenyl, 2- or 4-hydroxyphenyl.

Preferred sidechain portions of the structure of formula I are those wherein
$R_2$ is hydrogen, and $R_1$ is hydrogen.
$R_2$ is

$R_1$ is hydrogen, and $R_3$ is lower alkyl.

The products of formula I wherein the proline ring is monosubstituted give rise to cis-trans isomerism. The configuration of the final product will depend upon the configuration of the $R_4$ and $R_9$ substituent in the proline starting material. In general, it is preferred that the $R_4$ and $R_9$ substituents be in the cis configuration with respect to the carboxyl group of the proline residue.

The compounds of this invention form basic salts with a variety of inorganic or organic bases. The salt forming ion derived from such bases can be metal ions, e.g., aluminum, alkali metal ions, such as sodium or potassium, alkaline earth metal ions, such as calcium or magnesium, or an amine salt ion, of which a number are known for this purpose, for example, ammonium salts, aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantane, benzathine, or salts derived from amino acids like arginine, lysine or the like. The non-toxic physiologically acceptable salts like the sodium or potassium salts can be used medicinally as described below and are preferred. Although other salts which are not necessarily physiologically acceptable are useful in isolating or purifying a product acceptable for the purposes described below. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Compounds of formula I wherein $R_2$ is

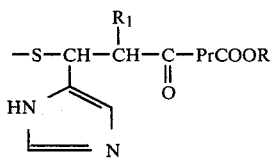

are produced by direct oxidation of a compound of formula I in which $R_2$ is hydrogen, e.g., with iodine, to obtain the symmetrical compound.

As shown in formula I, there is an asymmetric center in the proline ring which is in the L-configuration. The imidizole substituted carbon is asymmetric. Of course and additional asymmetric center can be present in the mercapto sidechain depending upon the $R_1$ substituent. The products of formula I can accordingly exist in stereoisomeric forms or as racemic mixtures thereof. All of these are within the scope of the invention. The synthesis described herein can utilize the racemate or one of the enantiomers as starting materials. When the racemic starting material is used in the synthesis procedure, the stereoisomers obtained in the final product can be separated by conventional chromatographic or fractional crystallization methods.

The compounds of formula I including their pharmaceutically acceptable salts are useful as hypotensive agents. They inhibit the conversion of the decapeptide angiotensin I to angiotensin II and, therefore, are useful in relieving angiotensin related hypertension. The action of the enzyme renin on angiotensin, a pseudoglobulin in blood plasma produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds, of formula I angiotensin dependent hypertension in the species of mammal suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg mammal) a total daily dosage of about 30 to 600 mg, preferably about 30 to 300 mg, of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, bendroflumethiazide, methclothiazide, trichlorothiazide, polythiazide or benthiazide, as well as ethacrynic acid, ticrynafen, chlorthalidone furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg of a compound of formula I is compounded with a physiologically acceptable vehicle, carrier excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrated process details are set forth in the following examples for the various reactions. These examples are preferred embodiments and also serve as models for the preparation of other compounds of this invention. The temperatures are given in degrees on the centigrade scale.

EXAMPLE 1

(±)-[3-(1H-Imidazol-4-yl)-3-mercapto-1-oxopropyl]-L-proline (a) t-Butyloxy carbonyl-urocanic Acid Urocanic acid (14.5 g, 0.105 mol) is dissolved in 52.5 ml of 2 N aqueous NaOH and lyophillized overnight. The resulting solid is dissolved in 20 ml of water and the solution obtained is treated with 30 ml of t-butanol followed by 25.2 g (0.116 mol) of di-tert-butyl carbonate added over a fifteen minute period. The reaction is stirred at room temperature overnight, then diluted with 120 ml of water and rinsed with two 30 ml portions of petroleum ether. The aqueous solution is then chilled in an ice bath, treated with 18 g of $KHSO_4$, the solution stirred for thirty minutes at room temperature and filtered. The solid obtained is rinsed with a small amount of absolute ethanol and dried to give 32.0 g of crude product. The crude solid is treated with 650 ml of boiling ethyl acetate and filtered hot. The filtrate is then stripped to dryness to yield 21.0 g (84%) of t-butyloxy carbonyl urocanic acid melting point (transition at 155° C.) 218°–219° C.

(b) t-Butyloxy Carbonyl Urocanic Acid, p-Nitrophenol Ester

A suspension of 23.1 g (97 mmol) of t-butyloxy carbonyl-urocanic acid, 13.4 g (97) mmol) of p-nitrophenol and 1 g of p-dimethylaminopyridine (DMAP) in 150 ml of $CH_2Cl_2$ is cooled in an ice bath and treated with 20.0 g (97 mmol) of dicyclohexylcarbodiimide. The ice bath is removed and the reaction stirred at room temperature overnight. The reaction mixture is filtered and rinsed with 50 ml portions of 0.1 N HCl, water, saturated $NaHCO_3$ and twice with brine. The solution is dried ($Na_2SO_4$), concentrated in vacuo and triturated with hot $CHCl_3$-hexanes to afford 28.3 g (81%) of t-butyloxy carbonyl urocanic acid, p-nitrophenol ester melting point 158°–159° C. (d).

(c) t-Butyloxy carbonyl urocanyl-L-proline t-butyl ester

A solution of 12.9 g (70.4 mmol) of L-proline, t-butyl ester and 9.8 ml (69.4 mmol) of triethylamine in 150 ml of $CH_2Cl_2$ is cooled in an ice bath under nitrogen and treated with 25 g (69.4 mmol) of t-butyloxy carbonyl urocanic acid, p-nitrophenol ester added in three portions over a thirty minute period. The reaction is allowed to warm to room temperature overnight, then diluted with 750 ml of ethyl acetate and rinsed with portions of 1 N aqueous $NH_4OH$ totaling 1.5 liters. The ethyl acetate solution is finally washed with brine, 10% $KHSO_4$, saturated $NaHCO_3$, brine, dried ($Na_2SO_4$) and concentrated in vacuo. The crude solid is recrystallized from 4 liters of 1:1, diethylether:hexanes to afford 6.2 g of product (melting point 124°–125° C.) in the first crop. Concentration of the mother liquor yielded 15.0 g (melting point 124°–125° C.) of product bringing the total yield to 21.2 g (78%) of t-butyloxy carbonyl urocanyl-L-proline t-butyl ester [α]$_D$ = −56.8° (c=1, CHCl$_3$).

(d)
(±)-1-[3-(Acetylthio)-3-[1-[(1,1-dimethylethoxy)-carbonyl]-1H-imidazol-4-yl]-1-oxopropyl]-L-proline, 1,1-dimethylethyl ester To a solution of 6 g (15.3 mmol) of t-butyloxy carbonyl-urocanyl-L-proline, t-butyl ester in 18 ml of CH$_2$Cl$_2$ cooled in an ice-water bath under nitrogen is added 3 ml (41 mmol) of thiolacetic acid. The cooling bath is removed and the stoppered reaction mixture is stirred overnight at room temperature. After removal of volatiles in vacuo, the crude reaction mixture was chromatographed using 140 g of E. Merck 9385 silica gel eluted with 30:1, diethyl ether:methanol under pressure. The product containing fractions are pooled to give 6.1 g (85%) of (±)-1-[3-(acetylthio)-3-[1-[(1,1-dimethylethoxy)-carbonyl]-1H-imidazol-4-yl]-1-oxopropyl]-L-proline, 1,1-dimethylethyl ester as an oil with some minor impurities by analytic tlc: tlc, R$_f$=0.34 on silica gel, 30:1 diethyl ether:methanol H-nmr (CHCl$_3$).

(e)
(±)-1-[3-(Acetylthio)-3-(1H-imidazol-4-yl)-1-oxopropyl]-L-proline, hydrochloride A solution of 2.8 g (5.99 mmol) of (±)-1-[3-(acetylthio)-3-[1-[(1,1-dimethylethoxy)carbonyl]-1H-imidazol-4-yl]-1-oxopropyl]-L-proline, 1,1-dimethylethyl ester in 125 ml of CH$_2$Cl$_2$ and 6.5 ml (59.9 mmol) of anisole is cooled in an ice-water bath under nitrogen and saturated with HCl. The cold bath is removed and the stoppered flask is kept at ambient temperature for five hours. The reaction mixture is then concentrated in vacuo and the residue partitioned between 40 ml of water and 40 ml of diethyl ether. The organic solution is extracted with 20 ml more of water and the combined aqueous extracts lyophillized to afford 1.9 g of a glassy solid. This material is chromatographed on about 600 ml of LH-20 eluted with water. Pooling of the product fractions (R=0.36 on silica gel; 4:1:1:1, n-butanol:pyridine:acetic acid:water) yielded 1.9 g of product (±)-1-[3-(acetylthio)-3-(1H-imidazol-4-yl)-1-oxopropyl]-L-proline, hydrochloride.

(f)
(±)-[3-(1H-Imidazol-4-yl)-3-mercapto-1-oxopropyl]-L-proline

A solution of 1.9 g (4.91 mmol) of S-acetyl compound (±)-1-[3-(acetylthio)-3-(1H-imidazol-4-yl)-1-oxopropyl]-L-proline, hydrochloride in 12 ml of water is added dropwise over a period of five minutes to 25 ml of 2 N aqueous NaOH cooled in an ice-bath under a flow of argon. The reaction is kept cold for ten minutes, then the bath is removed for five minutes. At the end of this time the reaction mixture is directly applied to a 90 ml Bio-Rex 70 (H+) column (ca. 300 meqv exchange capacity) and the product eluted with water under an atmosphere of nitrogen. After several early fractions showing pH ~5.0 the eluant pH fell to 2.0 (elution of HCl) then rose to pH 4.6-4.8 concurrent with the elution of the desired compound as confirmed by analytical tlc. The product containing fractions are pooled and lyophillized affording 1.2 g (87%) of (±)-[3-(1H-imidazol-4-yl)-3-mercapto-1-oxopropyl]-L-proline as a hydrate.

EXAMPLE 1A
±-[3-(1H-Imidazol-4-yl)-3-mercapto-2-methyl-1-oxopropyl]-L-proline (a) (E,Z)-3-(1H-Imidazol-4-yl)-2-methyl-2-propenoic acid, methyl ester A solution of 0.961 g (10 mmol) of methyl 2-(triphenylphosphoranylidene)propionate [H. J. Bestmann and H. Schulz, Angew. Chem., 73, 27 (1961)] and 3.48 g (10 mmol) of imidazole-4-carboxaldehyde [F. L. Pyman, J. Chem. Soc., 186 (1916)] in 50 ml of absolute ethanol is stirred at room temperature for seven days. At the end of this time, the ethanol is removed in vacuo and the desired product is isolated free of triphenylphosphine oxide by chromatography on silica gel. The product thus obtained is a mixture of E and Z olefin isomers.

(b) (E,Z)-3-(1H-Imidazol-4-yl)-2-methyl-2-propenoic acid

A solution of 1.66 g (10 mmol) of ester (E,Z)-3-(1H-imidazol-4-yl)-2-methyl-2-propenoic acid, methyl ester in 20 ml of dioxane at room temperature is treated with 10 ml of 1 N aqueous sodium hydroxide. The reaction mixture is stirred overnight at room temperature, then diluted with water and the unreacted starting material removed by extraction with ethyl acetate. The aqueous solution is concentrated in vacuo then applied to a 30 ml (100 meqv.) Bio-Rex 70 cation exchange resin column packed in 10% aqueous methanol in the H⊕ (acid) form. Elution with 10% aqueous methanol gives a first fraction of hydrochloric acid. Subsequently, the desired product is eluted and isolated as a mixture of E and Z olefin isomers after removal of the solvents in vacuo.

(c) ±-[3-(1H-Imidazol-4-yl)-3-mercapto-2-methyl-1-oxopropyl]-L-proline

By following the procedure of Example 1 but substituting (E,Z)-3-(1H-imidazol-4-yl)-2-methyl-2-propenoic acid in place of urocanic acid then ±-[3-(1H-imidazol-4-yl)-3-mercapto-2-methyl-1-oxopropyl]-L-proline is obtained.

EXAMPLES 2-34

By following the procedure of Example 1 but using a proline of Column I in place of the L-proline, t-butyl ester of Example 1(c); and using the t-butyloxy carbonyl p-nitrophenol ester compound of Column II in place of the t-butyloxy carbonyl urocanic acid p-nitrophenol ester of Example 1(c); and using the thiol compound of Column III in place of the thiolacetic acid of Example 1(d); then the product of Column IV is obtained. Hydrolysis of this compound according to the procedure of Example 1(f) yields the product of Col. V.

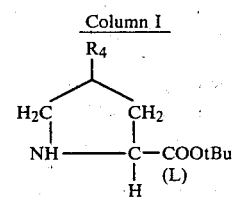

Column I wherein t Bu is a t-butyl group.

Column II

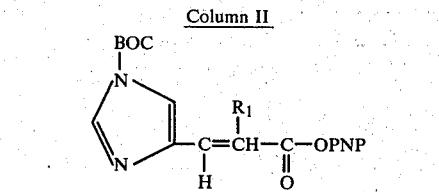

wherein BOC is t-butyloxy carbonyl and OPNP is a p-nitrophenol group

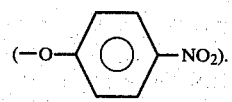

Column III $$R_3-\overset{\overset{O}{\|}}{C}-S$$

Column IV

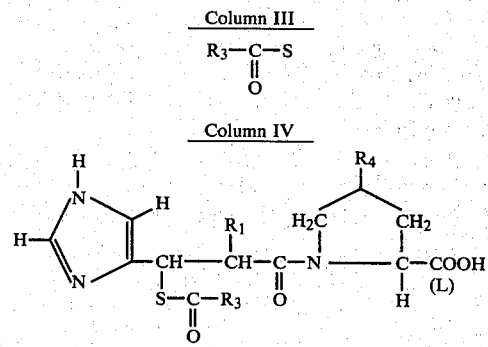

Column V

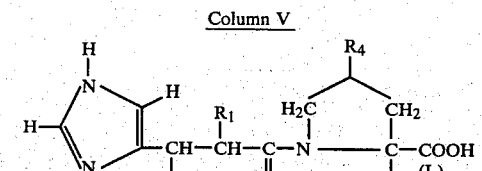

| Example | $R_1$ | $R_3$ | $R_4$ |
|---|---|---|---|
| 2 | —CH$_3$ | —CH$_3$ | —H |
| 3 | —H | —CH$_3$ | —CH$_3$ |
| 4 | —H | —CH$_3$ | —C$_2$H$_5$ |
| 5 | —CH$_3$ | —CH$_3$ | —CH$_3$ |
| 6 | —H | —CH$_3$ | —Cl |
| 7 | —H | —CH$_3$ | =O |
| 8 | —H | —CH$_3$ | —N—N=N |
| 9 | —H | —CH$_3$ | -CH(CH$_2$CH$_2$)(CH$_2$CH$_2$)CH$_2$ |
| 10 | —H | —CH$_3$ | —C$_6$H$_5$ |
| 11 | —H | —CH$_3$ | —C$_6$H$_4$—Cl |
| 12 | —H | —CH$_3$ | —CH$_2$—C$_6$H$_5$ |
| 13 | —H |  | —C$_6$H$_5$, —CH$_2$—C$_6$H$_4$—Cl |
| 14 | —H |  | —C$_6$H$_5$, —O—C(=O)—NH$_2$ |
| 15 | —H | —C$_6$H$_5$ | —O—C(=O)—N(CH$_3$)$_2$ |
| 16 | —H | —C$_6$H$_5$ | —OH |
| 17 | —H | —C$_6$H$_5$ | —OCH$_3$ |
| 18 | —H | —C$_6$H$_5$ | —SCH$_3$ |
| 19 | —H | —C$_6$H$_5$ | —O—CH$_2$—CH=CH$_2$ |
| 20 | —H | —C$_6$H$_5$ | —O—CH$_2$—C≡CH |
| 21 | —H | —CH$_3$ | —O—C$_6$H$_5$ |
| 22 | —H | —CH$_3$ | —O—C$_6$H$_4$—Cl |
| 23 | —H | —CH$_3$ | —O—CH$_2$—C$_6$H$_5$ |
| 24 | —H | —CH$_3$ | —O—CH$_2$—C$_6$H$_4$—Cl |
| 25 | —H | —CH$_3$ | —O—C$_6$H$_4$—C$_6$H$_5$ |
| 25A | —H | —CH$_3$ | —S—C$_6$H$_4$—C$_6$H$_5$ |
| 26 | —H | —CH$_3$ | —O-naphthyl |
| 26A | —H | —CH$_3$ | —S-naphthyl |
| 27 | —C$_2$H$_5$ | —CH$_3$ | —H |
| 28 | —H | —CH$_3$ | —CH$_3$ |
| 29 | —H | —CH$_3$ | —H |
| 30 | —H | —C$_6$H$_5$ | —H |
| 31 | —H | —CH$_2$—C$_6$H$_5$ | —H |
| 32 | —H | —CH$_3$ | —S—C$_6$H$_5$ |
| 33 | —CH$_3$ | —C$_6$H$_5$ | —S—C$_6$H$_4$—F |
| 34 | —H | —C$_6$H$_5$ | —S—C$_6$H$_5$ |

EXAMPLES 35–46

By following the procedure of Example 1 but using a proline of Column I in place of the L-proline, t-butyl ester of Example 1(c); and using the t-butyloxy carbonyl p-nitrophenol ester compound of Column II in place of the t-butyloxy carbonyl urocanic acid p-nitrophenol ester of Example 1(c); and using the thiol compound of Column III in place of the thiolacetic acid of Example 1(d); then the product of Column IV is obtained. Hydrolysis of this compound according to the procedure of Example 1(f) yields the product of Column V.

Column I

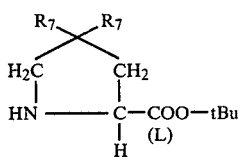

wherein t Bu is a t-butyl group.

Column II

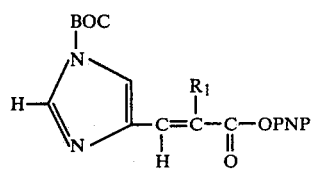

wherein BOC is t-butyloxy carbonyl and OPNP is a p-nitrophenol group.

Column III

Column IV

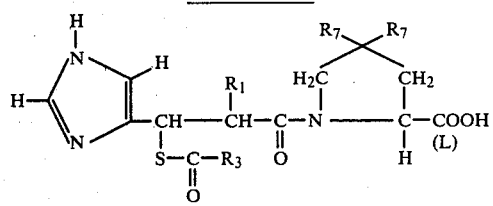

Column V

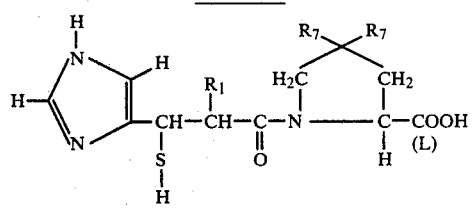

| Example | $R_1$ | $R_3$ | $R_7$ |
|---|---|---|---|
| 35 | —H | —CH$_3$ | —Cl |
| 36 | —H | —CH$_3$ | —Br |
| 37 | —H | —CH$_3$ | —F |
| 38 | —H | —CH$_3$ | —O—CH$_3$ |
| 39 | —H | —CH$_3$ | —O—⟨phenyl⟩ |
| 40 | —H | —CH$_3$ | —O—CH$_2$—⟨phenyl⟩ |
| 41 | —H | —CH$_3$ | —O—CH$_2$—⟨phenyl⟩—Cl |
| 42 | —H | ⟨phenyl⟩ | —O—⟨biphenyl⟩ |
| 42A | —H | ⟨phenyl⟩ | —S—⟨biphenyl⟩ |
| 43 | —CH$_3$ | ⟨phenyl⟩ | —O—⟨naphthyl⟩ |
| 43a | —H | ⟨phenyl⟩ | —S—⟨naphthyl⟩ |
| 44 | —CH$_3$ | ⟨phenyl⟩ | —Cl |
| 45 | —H | —CH$_3$ | —O—CH$_3$ |
| 46 | —H | —CH$_3$ | —O—⟨phenyl⟩ |

EXAMPLES 47-52

Following the procedure of Example 1 but using a proline of Column I in place of the L-proline, t-butyl-ester of Example 1(c), and using the t-butyloxy carbonyl p-nitrophenol ester compound of Column II in place of the t-butyloxy carbonyl urocanic acid p-nitrophenol ester of Example 1(c); and using the thiol compound of Column III in place of the thiolacetic acid of Example 1(d); then the product of Column IV is obtained. Hydrolysis of this compound according to the procedure of Example 1(f) yields the product of Column V.

Column I (wherein t-Bu is a t-butyl group).

Column II wherein BOC is t-butyloxy carbonyl and OPNP is p-nitrophenol group.

Column III

Column IV

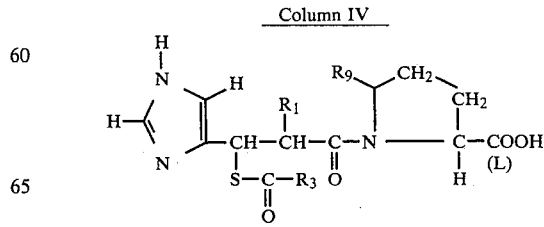

Column V

-continued

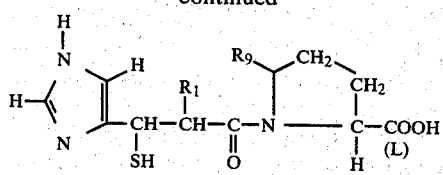

| Example | $R_1$ | $R_3$ | $R_9$ |
|---------|-------|-------|-------|
| 47 | —H | —CH$_3$ | =O |
| 48 | —H | —CH$_3$ | 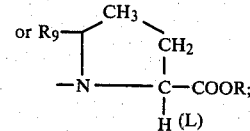 |
| 49 | —H | —CH$_3$ | 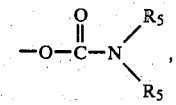 |
| 50 | —H | 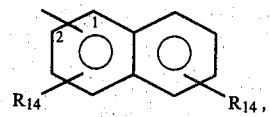 | =O |
| 51 | —CH$_3$ | —CH$_2$—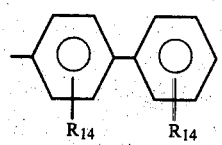 | 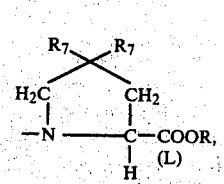 |
| 52 | —CH$_3$ | —CH$_3$ | 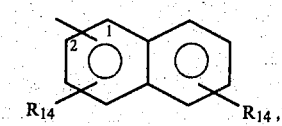 |

What is claimed is:

1. A compound of the formula

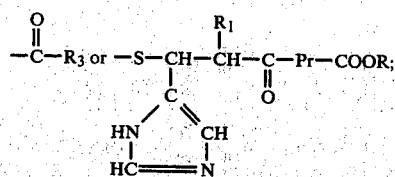

wherein

R is hydrogen or lower alkyl;

$R_1$ is hydrogen, lower alkyl, or halo substituted lower alkyl;

$R_2$ is hydrogen,

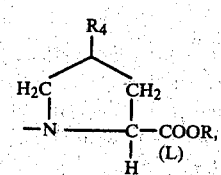

$R_3$ is lower alkyl, phenyl, or phenyl-lower alkyl;

Pr-COOR is a substituted or unsubstituted proline of the structures

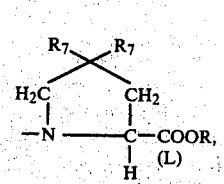 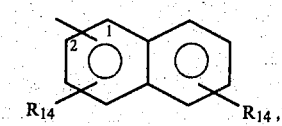

or $R_9$ is $R_4$ is hydrogen, lower alkyl, hydroxy, halogen, keto, azido, a saturated cycloalkyl ring of 3 to 7 carbons, -Y-R$_6$, phenyl, phenyl-lower alkyl, substituted phenyl, or substituted phenyl-lower alkyl wherein said phenyl substituent is lower alkyl, lower alkoxy, lower alkylthio, Cl, Br, F, or hydroxy;

$R_5$ is hydrogen or lower alkyl;

Y is oxygen or sulfur;

$R_6$ is lower alkyl, lower alkenyl, lower alkynyl, phenyl, phenyl-lower alkyl, substituted phenyl or substituted phenyl-lower alkyl wherein said phenyl substituent is lower alkyl, lower alkoxy, lower alkylthio, Cl, Br, F, or hydroxy, substituted or unsubstituted 1- or 2-naphthyl of the formula or substituted or unsubstituted biphenyl of the formula wherein $R_{14}$ is hydrogen, methyl, methoxy, methylthio, Cl, Br, F, or hydroxy;

$R_7$ is halogen or -Y-R$_8$;

$R_8$ is lower alkyl, phenyl, phenyl-lower alkyl, substituted phenyl-lower alkyl wherein said phenyl substituent is lower alkyl, lower alkoxy, lower alkylthio, Cl, Br, F, or hydroxy, substituted or unsubstituted 1- or 2-naphthyl of the formula substituted or unsubstituted biphenyl of the formula

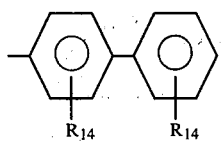

wherein R$_{14}$ is as defined above, or when the R$_8$ groups are lower alkyl they join to complete an unsubstituted 5- or 6-membered ring or such ring wherein a carbon atom is substituted by a lower alkyl or di(lower alkyl) group; and R$_9$ is keto, phenyl, 2- or 4-hydroxyphenyl; or a salt thereof.

2. The compound of claim 1 wherein
R is hydrogen or lower alkyl;
R$_1$ is hydrogen or lower alkyl;
R$_2$ is hydrogen, or

R$_3$ is lower alkyl, phenyl or phenyl lower alkyl;
R$_4$ is hydrogen, lower alkyl, cyclohexyl,

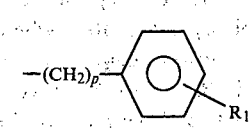

or Y-R$_6$;
R$_6$ is lower alkyl of 1 to 4 carbons,

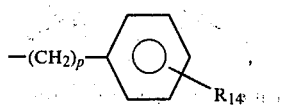

a substituted or unsubstituted 1- or 2-naphthyl of the formula

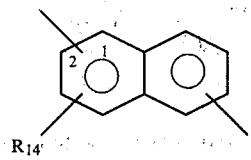

or a substituted or unsubstituted biphenyl of the formula

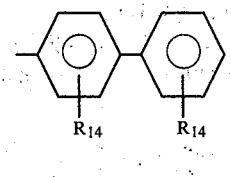

p is zero, one or two;
R$_{14}$ is hydrogen, methyl, methoxy, methylthio, Cl, F, Br, or hydroxy;
R$_7$ is Cl, F, or -Y-R$_8$;
R$_8$ is lower alkyl of 1 to 4 carbons or the R$_8$ groups join to complete an unsubstituted 5- or 6-membered ring or said ring in which one or more of the carbons has a methyl or dimethyl substituent;
R$_9$ is phenyl, 2- or 4-hydroxyphenyl;
or a salt thereof.

3. The compound of claim 2, [3-(1H-imidazol-4-yl)-3-mercapto-1-oxopropyl]-L-proline.

4. A composition for treating hypertension comprising a pharmaceutically acceptable carrier and a pharmaceutically effective amount of a hypotensive agent or pharmaceutically acceptable salt thereof of the formula

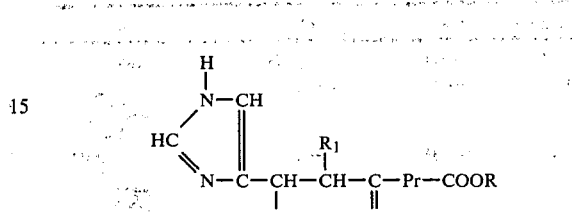

wherein
R is hydrogen or lower alkyl;
R$_1$ is hydrogen, lower alkyl, or halo substituted lower alkyl;
R$_2$ is hydrogen,

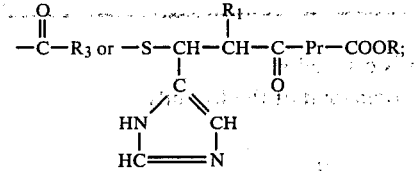

R$_3$ is lower alkyl, phenyl, or phenyl-lower alkyl;
Pr-COOR is a substituted or unsubstituted proline of the structures

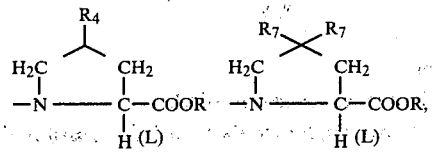

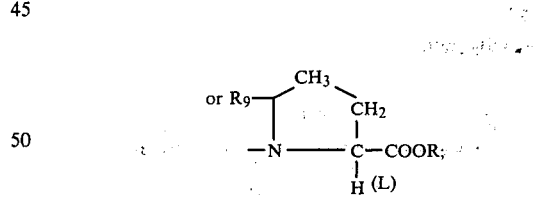

R$_4$ is hydrogen, lower alkyl, hydroxy, halogen, keto, azido, a saturated cycloalkyl ring of 3 to 7 carbons,

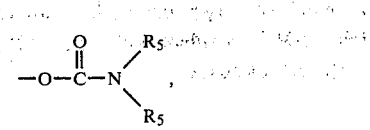

-Y-R$_6$, phenyl, phenyl-lower alkyl, substituted phenyl, or substituted phenyl-lower alkyl wherein said phenyl substituent is lower alkyl, lower alkoxy, lower alkylthio, Cl, Br, F, or hydroxy;
R$_5$ is hydrogen or lower alkyl;
Y is oxygen or sulfur;

$R_6$ is lower alkyl, lower alkenyl, lower alkynyl, phenyl, phenyl-lower alkyl, substituted phenyl or substituted phenyl-lower alkyl wherein said phenyl substituted is lower alkyl, lower alkoxy, lower alkylthio, Cl, Br, F, or hydroxy, substituted or unsubstituted 1- or 2-naphthyl of the formula

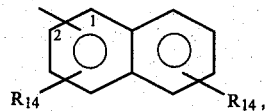

or substituted or unsubstituted biphenyl of the formula

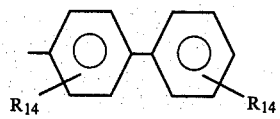

wherein $R_{14}$ is hydrogen, methyl, methoxy, methylthio, Cl, Br, F, or hydroxy;

$R_7$ is halogen or $-Y-R_8$;

$R_8$ is lower alkyl, phenyl, phenyl-lower alkyl, substituted phenyl-lower alkyl wherein said phenyl substituent is lower alkyl, lower alkoxy, lower alkylthio, Cl, Br, F, or hydroxy, substituted or unsubstituted 1- or 2-naphthyl of the formula

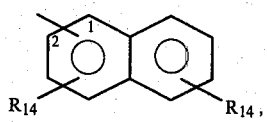

substituted or unsubstituted biphenyl of the formula

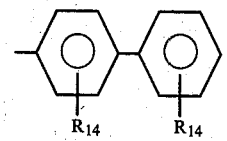

wherein $R_{14}$ is as defined above, or when the $R_8$ groups are lower alkyl they join to complete an unsubstituted 5- or 6-membered ring or such ring wherein a carbon atom is substituted by a lower alkyl or di(lower alkyl) group; and $R_9$ is keto, phenyl, 2- or 4-hydroxyphenyl.

5. The composition of claim 4 also including an antihypertensive diuretic.

6. The method of alleviating hypertension which comprises administering to a mammalian specie an effective amount of the composition of claim 4.

UNITED STATES PATENT OFFICE
CERTIFICATE OF CORRECTION

PATENT NO. : 4,313,948
DATED : February 2, 1982
INVENTOR(S) : Miguel Angel Ondetti, Denis E. Ryono It is certified that error appears in the above-identified patent and that said Letters Patent are hereby corrected as shown below:

In the Abstract, in the definition of $R_2$ after "or" should be inserted

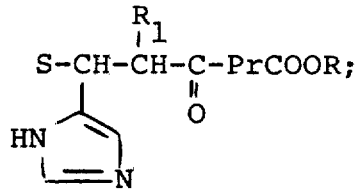

Col. 18, first formula should read

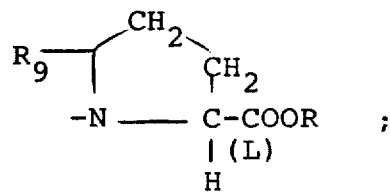

Col. 20, fifth formula should read

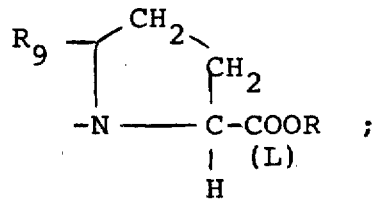

Signed and Sealed this

*Twenty-sixth* Day of *October 1982*

[SEAL]

Attest:

GERALD J. MOSSINGHOFF

*Attesting Officer*  *Commissioner of Patents and Trademarks*